United States Patent [19]

Snoke et al.

[11] 4,055,469

[45] Oct. 25, 1977

[54] PURIFICATION OF MICROBIAL ENZYME EXTRACTS USING SYNTHETIC POLYELECTROLYTES

[75] Inventors: Roy Eugene Snoke, Webster; Gerald Wayne Klein, Pittsford, both of N.Y.

[73] Assignee: Eastman Kodak Company, Rochester, N.Y.

[21] Appl. No.: 749,647

[22] Filed: Dec. 10, 1976

[51] Int. Cl.$^2$ ............................................. C07G 7/028
[52] U.S. Cl. ................................................. 195/66 R
[58] Field of Search .................. 195/66 R, 66 A, 66 B

[56] References Cited

U.S. PATENT DOCUMENTS

| | | | |
|---|---|---|---|
| 3,252,961 | 5/1966 | Rodgers et al. | 260/112 R |
| 3,555,001 | 1/1971 | Waliis et al. | 260/112 R |
| 3,725,545 | 4/1973 | Maes | 424/180 |
| 3,728,224 | 4/1973 | Borglum | 195/66 R |
| 3,737,377 | 6/1973 | Sternberg | 195/66 R |
| 3,794,562 | 2/1974 | Bergmeyer et al. | 195/66 R |
| 3,846,543 | 11/1974 | Fields et al. | 424/89 |

FOREIGN PATENT DOCUMENTS

| | | | |
|---|---|---|---|
| 1,411,503 | 10/1975 | United Kingdom | 195/66 R |

OTHER PUBLICATIONS

Abstract of Belgium Patent No. 754,018.
Abstract of Japanese Patent No. 73/33387.
Abstract of East German Patent No. 105,251.
Katchalsky, Endeavor, vol. 12, pp. 90–94 (1953).

*Primary Examiner*—Lionel M. Shapiro
*Attorney, Agent, or Firm*—George W. Neuner

[57] ABSTRACT

Nucleic acids and unwanted proteins are removed from microbial enzyme extracts by precipitation with water-soluble, cationic polymers comprised of monomers having the structure

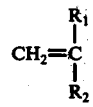

wherein $R_1$ is a hydrogen atom, a lower alkyl group, or the equivalent and $R_2$ is a nitrogen containing group capable of carrying a positive electrical charge when the polymer is dissolved in an aqueous solution.

14 Claims, 9 Drawing Figures

OPEN BARS = ENZYME ACTIVITY

SHADED BARS = NUCLEIC ACID

PURIFICATION OF MICROBIAL ENZYME EXTRACTS USING SYNTHETIC POLYELECTROLYTES

FIELD OF THE INVENTION

This invention is related to the purification of enzyme preparations and particularly to the removal of nucleic acids and unwanted protein from microbial enzyme extracts.

DESCRIPTION OF THE PRIOR ART

Purification of enzymes from microbial extracts is complicated by the presence of nucleic acids which interfere with salt fractionation or chromatographic procedures that commonly are used in enzyme purification. Several methods have been developed to remove nucleic acids from crude cell extracts by precipitation, for example, complexing the negatively-charged acids with positively charged materials such as protamine sulfate, streptomycin sulfate, or manganese chloride.

However, problems have been experienced with each of these methods. For example, protamine sulfate, a small protein containing arginine residues has been isolated only from the sperm of certain fish, and in application, this protein is difficut to dissolve in water. In addition, problems with reproducing results have been reported by Oxenburgh and Snoswell Nature, Vol. 207, p. 1416 (1965). Stretomycin sulfate, an antibiotic containing the diguanido base streptidine is generally more consistent in use, but the extent of precipitation of nuclei acids is influenced by various electrolytes in the extract. In fact, precipitation of DNA by streptomycin is prevented by phosphate buffer; inhibition is ion concentration and solution pH dependent. Manganese chloride is inexpensive and convenient to use, but is less advantageous than the others in that addition of this salt frequently results in loss of enzyme activity.

Enzymatic degradation of nucleic acids by nucleases could by used, but this step would add additional material to the extract or require the development of an insolubilized enzyme system, a costly step. Ion exchange chromatography also has been used to separate protein and nucleic acids, but it is not a convenient or simple process for large scale enzyme purification.

Therefore a continuing need is felt for more advantageous methods for removing nucleic acids for microbial enzyme extracts.

Nucleic acids, as well as proteins and any watersoluble, electrical charge-carrying polymers, are defined as polyelectrolytes by Katchalsky in "Polyelectrolytes", Endeavor, Vol. 12, page 90 (1953). He suggests that strong interactions occur between polyelectrolytes of opposite charge and that such interactions could result in mutual precipitation.

Various suggestions for precipitating impurities from enzyme solutions have been made in the prior art. For example, U.S. Pat. No. 3,728,224 and British Pat. No. 1,411,503 described the use of cationic surfactants such as quaternary ammonium compounds to precipitate impurities including nucleic acids and protein from enzyme solutions. The treatment of enzyme solutions produced by Streptomyces rectus with a polyoxyethylenealkylamine is described in Japanese Pat. No. 73/33387. U.S. Pat. No. 3,737,377 describes the use of polyacrylic acid to precipitate the enzyme lactase from solution in order to purify it.

U.S. Pat. No. 3,252,961 describes the use of anionic polyelectrolytes to flocculate and separate protein from whey. Clarification of fermentation broths using a flocculant that is the reaction product of polyfunctional amine with a halogenated epoxide or a polyvinylimidazole containing units prepared by modifying nitrite polymers is described by Belgian Pat. No. 754,018. East German Pat. No. No. 105,251 describes cationic esters of polyacrylic acid with quaternary ammonium compounds and containing at least one alcoholic or phenolic group as useful for flocculating agents to separate bacterial cells from culture liquor.

U.S. Pat. Nos. 3,846,543 and 3,555,001 describe the use of water-insoluble polymers containing imide groups selected from diloweralkyliminoloweralkylimide groupings and loweralkylaminodi(loweralkylimide) linkages to separate virus from non-viral protein.

A method for enriching or purifying protein solutions using precipitation by polyethylene-imines is described by British Pat. No. 1,298,431. The precipitation of protein by this method using polyethylene-imines is dependent upon ion concentration. Furthermore, ethyleneimine itself is carcinogenic and polyethylene-imine may have harmful effects. Therefore polyethylene-imine is not considered to be a material of choice for commercial purification of enzymes.

A method for coating or complexing nucleic acids with DEAE-Dextran or other cationically charged polymers for enhancing the production of antibodies when introduced in conjunction with an antigen into an animal host is described in U.S. Pat. No. 3,725,545. For the purposes described in this reference, it is desired to maintain the complexed nucleic acids in solution and it is suggested that care must be taken less the complex precipitate under certain conditions.

SUMMARY OF THE INVENTION

The present invention provides a method for the purification of microbial enzyme extracts by the removal of nucleic acids and unwanted protein molecules using a class of cationic synthetic polymers. It is quite unexpected to discover a class of polymers that tend to selectively precipitate nucleic acid and unwanted protein molecules from microbial enzyme extracts leaving the desired enzyme in the extract. Among other advantages in using the polymers described herein for precipitating nucleic acids and non-active proteins from microbial extracts, the effectiveness of complex formation and precipitation using these polymers is not strongly influenced by the pH nor, at least up to about the value of pKa of the polymer, by the protein concentration of the extract.

The cationic synthetic polymers useful in this invention are soluble in water and are comprised of cationic monomers having the following structure

I wherein $R_1$ is a hydrogen atom or a lower alkyl group; and $R_2$ is a nitrogen containing group capable of carrying a positive electrical charge when the polymer is dissolved in an aqeuous solution having a pH value not greater than about the pKa of the polymer.

As used herein, the term "cationic" when applied to monomers and polymers described for in this invention means that the monomer or polymer is capable of carrying a charge when dissolved in an aqueous solution having a pH value that is below the pKa of the monomer or polymer described.

In accordance with the present invention, microbial enzyme extracts are purified by adding a quantity of one of the above-described polymers to the extract to precipitate impurities, i.e., nucleic acids and non-active protein. The amount to be added depends upon the charge density of the particular polymer and upon the amount of impurities in the extract. Conveniently, the amount of polymer added is based on the amount of protein in the extract.

DESCRIPTION OF THE INVENTION

According to the present invention, microbial enzyme extracts are purified using certain cationic polymers. When added to the extracts these polymers precipitate nucleic acids and non-active protein leaving the desired enzyme in a more purified extract.

We have discovered that a certain class of cationic, water-soluble polymers can be used to effectively remove nucleic acids and non-active proteins from microbial enzyme extracts. These water-soluble, cationic polymers are comprised of cationic monomers having the structure I with $R_1$ and $R_2$ as defined above. As used herein the term lower alkyl group is used to refer to any alkyl group, whether substituted or unsubstituted, that does not interfere with the desired function of the resulting polymer, i.e., the polymer must be water-soluble and cationic. Generally, such lower alkyl groups include those having from 1 to about 4 carbon atoms.

$R_2$ can be any nitrogen containing group capable of carrying a positive electrical charge when dissolved in an aqueous solution. Preferred groups include amine groups, particularly those containing a carbonyl or an oxycarbonyl group. Particularly useful groups for $R_2$ including the following:

where X is an anion, for example, a halide ion such as $Cl^\ominus$, $Br^\ominus$, etc., or an organosulfo containing anion such as $CH_3OSO_3^\ominus$, etc., or the equivalent.

Examples of cationic monomers useful in preparing the polymers of this invention include N-methyl-2-aminoethyl methacrylate hydrochloride, 1-vinylimidazole, 2-(N,N,N-trimethylammonium)ethyl methacrylate chloride, 2-(N,N-dimethylamino)ethyl methacrylate, 2-(N,N,N-trimethyl-ammonium)ethyl methacrylate methosulfate, and 2-hydroxy-3-(N,N,N-trimethylammonium)propyl methacrylate chloride.

While the mechanism is not completely understood, it is believed that precipitation results from strong electrostatic attraction between oppositely charged groups on the molecules, therefore, the effectiveness of a precipitant would be influences by the charge density of the molecules. The extent of ionization of the charged groups also would then be important, since more ionized polymers are probably in an extended rather than coiled configuration. Thus the polymers described in this invention are generally useful over a range of pH values at least up to the value of the pKa for the cationic polymer.

Copolymerization of the cationic monomers described herein with non-charge carrying monomers enables one to obtain polymers having a wide range of charge densities for practicing this invention. One or more of the monomers capable of carrying a positive charge may be copolymerized with other monomers which, at least under the conditions of use, are not capable of carrying a charge. For example, various vinyl monomers known to those skilled in the art of making vinyl polymers can be used. The only restrictions are that the non-charge carrying monomer not interfere with the cationic nature or water-solubility of the polymer so as to make it non-effective in the practice of this invention. Particularly useful monomers for copolymerizaing with the monomers having structure I are acrylamide and hydroxyalkyl acrylates such as, for example, 2-hydroxyethyl acrylate. Other equivalent monomers, however, would be equally suitable for copolymerization.

Microbial enzyme extracts are purified in accordance with the invention by adding a quantity of the above-described water-soluble, cationic polymer to the enzyme extract to precipitate nucleic acids and non-active proteins. These cationic polymers have been found useful in purifying extracts from a variety of microorganisms. A partial list includes, for example, M. flavins, B. megaterium, P. testeroni, and S. faecalis. The amount of polymer added to the enzyme extract is dependent upon the particular enzyme extract to be purified and upon the particular cationic polymer being used, etc. For example, a larger quantity of a polymer having a low charge density may be necessary to achieve as desirable a result as a smaller quantity of a polymer having a high charge density. Also a particular enzyme extract may be purified more effectively using a polymer having a low charge density or a high charge density. Generally, the polymers of this invention comprise at least 10 percent by weight, and preferably 20 percent by weight, of monomers having structure I in order to carry out effective purification without using unduly large quantities of polymer.

Conveniently the amount of polymer to be added to the enzyme extract is based upon the amount of protein in the extract. This is done because the amount of protein present in the extract can be conveniently estimated by a simple spectrophotometric technique described by Layne in Methods in Enzymology, Vol. 3, page 451 (1957). Generally adding an amount of polymer in the range of from about 0.01 to about 0.5 mg per mg of protein in the extract, and preferably from about 0.05 to about 0.2 mg per mg of protein, has been found to effectively remove nucleic acids and non-active proteins from the extract. It should be noted that equivalent results can be obtained by determining the quantity of cationic polymer to be added to the extract based on any other parameter of the enzyme extract, such as, for example, the quantity of nucleic acids present in the extract.

After adding the cationic polymer to the enzyme extract, the extract is incubated for a period of time while stirring in order to allow the polymer to complex with the nucleic acids and non-active proteins. Generally the incubation is carried out at low temperatures, for example 0 to 4° C is satisfactory, in order to preserve enzyme activity. Other temperatures may be selected depending upon the particular enzyme extract being treated. The period of incubation is not critical as long as it is sufficient to allow complexing to take place. Generally, about 30 minutes has been found satisfactory. The extract is then centrifuged to remove the precipitated impurities.

In the examples which are provided to further illustrate and clarify the invention, unless otherwise noted, the following definitions apply.

1. Polymers (Synthetic Polyelectrolytes)

| Polymer No. | Monomers | Monomer Ratio | % Solids | Bulk Viscosity (cps) |
|---|---|---|---|---|
| 1 | E:C | 20:80 | 10.5 | 705 |
| 2 | E:C | 40:60 | 10.7 | 99 |
| 3 | E:C | 40:60 | 10.6 | 375 |
| 4 | E:C | 60:40 | 10.7 | 554 |
| 4a | E:C | 60:40 | 10.6 | 6150 |
| 5 | E:C | 80:20 | 11.0 | 1400 |
| 5a | E:C | 80:20 | 11.0 | 4310 |
| 6 | E:C | 90:10 | 21.7 | 380 |
| 6a | E:C | 90:10 | 24.0 | 4500 |
| 7 | G:C | 95:05 | 13.6 | 1400 |
| 8 | G | 100 | 10.0 | high |
| 9 | H | 100 | 20.6 | 74 |
| 10 | F:C | 90:10 | 9.7 | 40 |
| 11 | A:D:C | 10:80:10 | 12.3 | 93 |
| 12 | A:B | 40:60 | 10.4 | 25 |
| 13 | EI | PEI-600* | 33 | 5000 |

*Polyethylenimine, commercial product from Dow Chemical Company, Midland, Michigan 2. Identification of Monomers

| Monomer | Name |
|---|---|
| A | Acrylamide |
| B | N-Methyl-2-aminoethyl methacrylate hydrochloride |
| C | 2-Hydroxyethyl acrylate |
| D | 1-Vinylimidazole |
| E | 2-(N,N,N-Trimethylammonium)ethyl methacrylate chloride |
| F | 2-(N,N-Dimethylamino)ethyl methacrylate |
| G | 2-(N,N,N-Trimethylammonium)ethyl methacrylate methosulfate |
| H | 2-Hydroxy-3-(N,N,N-Trimethylammonium)-propyl methacrylate chloride |
| EI | Ethylene-imine |

3. Production of Enzyme Extract a. Cell Growth

A microorganism isolated in the laboratory was grown in a medium containing 2 percent L-aspartate, 0.4 percent potassium phosphate, and basal salts: 250 mg magnesium sulfate, 17 mg manganese sulfate, 28 mg ferrous sulfate, 6 mg sodium sulfate, 10 mg calcium chloride, and 0.6 mg zinc sulfate per liter of growth medium. The final pH of the growth medium was 7.0. Flasks containing sterile media were innoculated then incubated at 30° C with mixing at 200 rpm for 24 hours. Cells were harvested by centrifugation at 13,700 × g for 20 minutes.

b. Cell-free Extract

Harvested cells were suspended in nine volumes of either 0.1 M potassium phosphate buffer, pH 7.0, containing 1.0 mM ethylenediamine tetraacetic acid and 1.0 mM dithiothreitol (DTT buffer) or in 0.15 M Tris-Cl buffer, pH 8.5. The suspension was cooled in a brine-ice bath, and cells were lysed by sonication. Cells and cell debris were removed by centrifugation at 27,000 × g for 15 minutes. The supernatant fraction was the cell-free extract.

4. Polymer Treatment

Aliquots of the extract were kept cool at 4° C and then polymer was added to the samples to give 0.2 mg polymer per mg protein, or as indicated; contol samples had an equal volume of water added instead of polymer. Samples were incubated at 4° C and constantly stirred with a magnetic stirrer for 30 minutes. The extracts were then centrifuged at 34,800 × g for 20 minutes; the clear, supernatant fraction was saved for assay.

5. Protein Assay

Protein was determined using the spectrophotometric method described by Layne, Methods in Enzymology, Vol. 3, page 451 (1957).

6. Nucleic Acid Assay

The ratio of 280 to 260 mμ absorbance gives an indication of the protein to nucleic acid ratio described by Layne, supra. In these crude extracts, the ratio generally was 0.73 or approximately 0.09 mg nucleic acid per mg protein. Values determined by this technique are not rigorous, but are found to be closely related to the actual values and they were used to follow changes in nucleic acid content of extracts following exposure to polymer.

7. Enzyme Assay

Aspartase, one of the major enzymes identified in the crude cell-free extracts, was selected to monitor enzyme activity in the examples using extracts from the laboratory isolated microorganism. Its activity was monitored by following the formation of fumarate at 240 nm (millimolar extinction coefficient was 2.53). Assay mixtures contained in 1.0 ml: 60.0 mM Tris-Cl buffer, pH 8.5, 1.8 mM magnesium sulfate, 0.09 mM ethylenediamine-tetraacetic acid, 50.0 mM L-aspartate, water and enzyme. Reactions were initiated by the addition of 0.01 units of enzyme, and the reaction temperature was 30° C. A unit is defined as that amount of aspartase required to produce 1 $\mu$mole of fumarate per minute.

EXAMPLE 1

Effect of Polymer Concentration and Charge Density on the Precipitate

Figure 1:
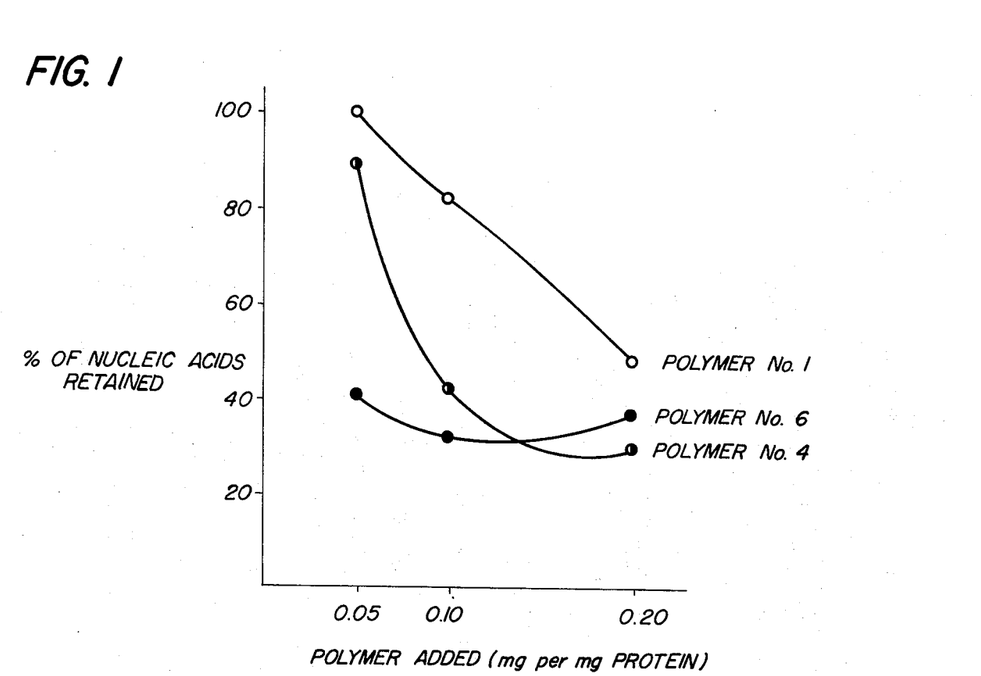
FIG. 1 is a graph illustrating the effect of polymer concentration on the removal of nucleic acid from enzyme extract for polymer as described herein having various charge densities.
Figure 2:
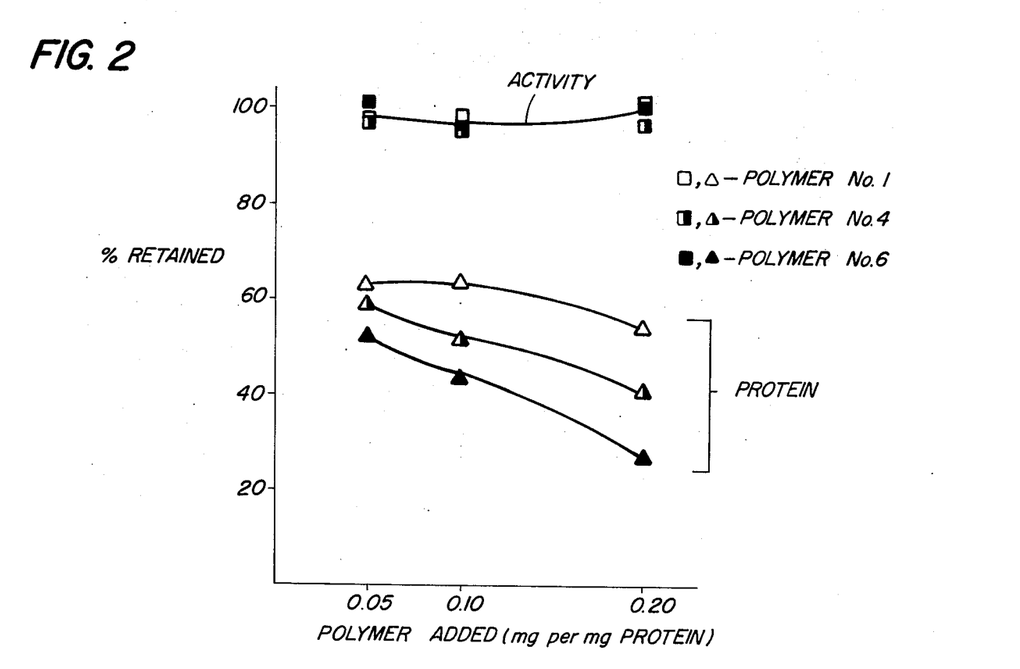
FIG. 2 is a graph illustrating the effectiveness of the polymers as described herein in selectively removing nonactive protein from an enzyme extract.
Figure 3:
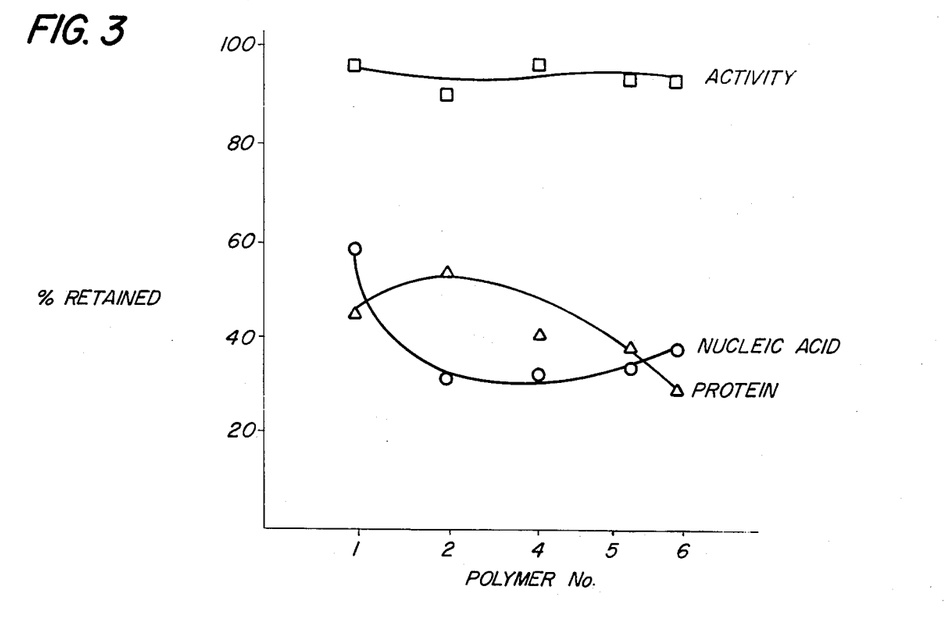
FIG. 3 is a graph illustrating the effectiveness of polymers as described herein having various charge densities in removing nucleic acid and non-active proteins from an enzyme extract.

A series of copolymers containing increasing amounts of the cationic monomer 2-(N,N,N-trimethylammonium)ethyl methacrylate chloride (E) and proportionately decreasing amounts of 2-hydroxyethyl acrylate (C) were synthesized, and the effectiveness of each polyelectrolyte was tested. A comparison of the extent of removal of nucleic acids is presented in FIG. 1. More nucleic acid was precipitated as the amount of polymer added to the sample was elevated; also, the effectiveness of the polyelectrolytes increased as the charged portion increased from 20 to 60 to 90 percent of the polymer. Protein in the extracts also was precipitated somewhat by these copolymers (FIG. 2), and this removal was polymer-concentration and charge-density dependent. However, no significant loss of enzyme activity occured with exposure to these copolymers within the range of polyelectrolyte concentrations tested. A comparison of the removal of nucleic acid, protein and aspartase activity by an extended series of polymers of varying charge densities is presented in FIG. 3. All polymers were used at 0.2 mg per mg protein. None of the polymers tested precipitated enzyme, but nucleic acids were removed with maximum precipitation when the cationic monomer was 40 percent or greater of the copolymer. As noted above, more purification of enzyme, i.e., greater activity per mg protein, was obtained with the more charged precipitants.

EXAMPLE 2

Effect of Polymer Size on the Precipitants

Figure 4:
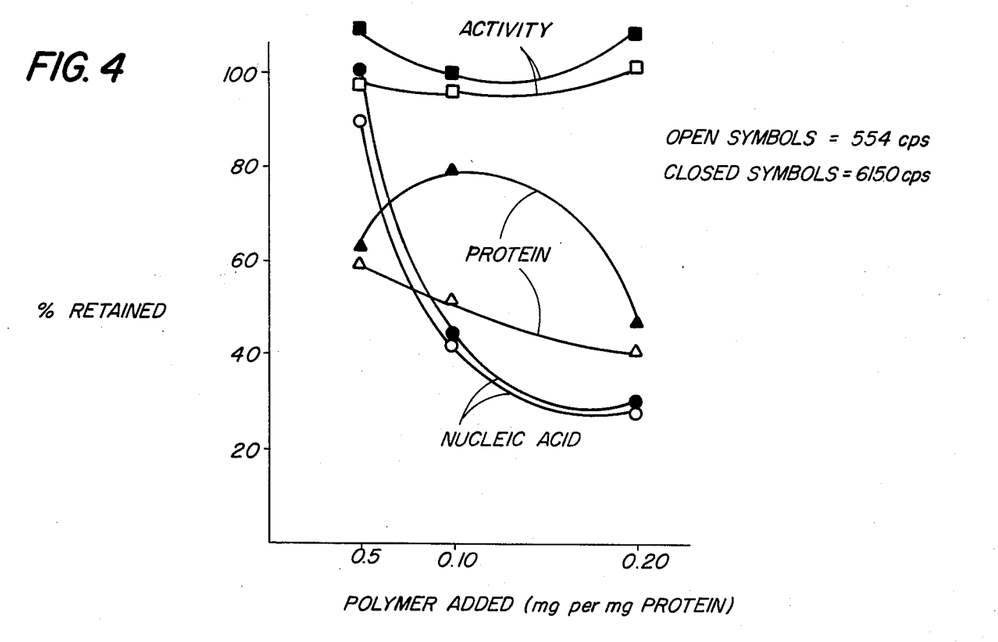
FIG. 4 is a graph illustrating the effect of the size of the polymers as descried herein on the removal of nucleic acids and non-active protein from an enzyme extract.

As indicated previously, although the mechanism of precipitation is not understood, it was theorized that removal of contaminants by this type of precipication requires that the polyelectrolytes combine, probably by molecular pairing, and most likely, the pair molecules are randomly twisted together rather than in regular spirals. The size of precipitants, therefore, could influence the extent and effectiveness of this complex formation. Polymer size relative to other polymers can be estimated by a comparision of sample viscosities, since viscosity increases with the length of the molecule. To investigate this possibility, two samples of polymer 4 with viscosities of 554 and 6150 centipoises (cps) were tested. No significant modification in the pattern of enzyme activity or nucleic acid precipitation was found when increasing concentrations of either of these copolymers were added to crude extracts (see FIG. 4). The amount of protein precipitated also was similar with both polymers.

EXAMPLE 3

Effect on Other Polymers on Precipitation

Figure 5:
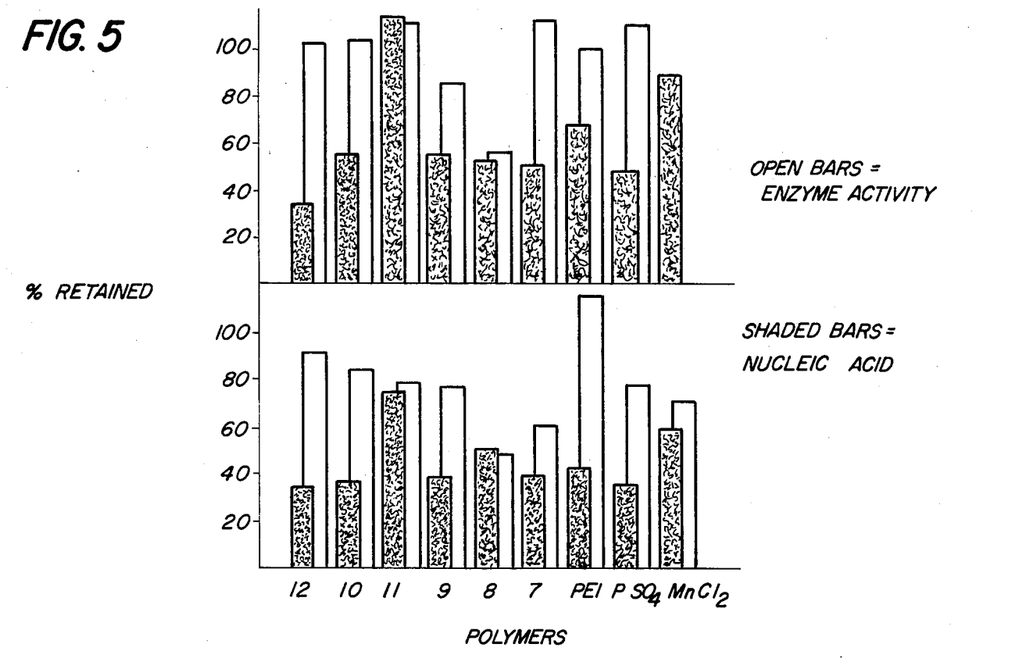
FIG. 5 is a graph illustrating the effectiveness of removing nucleic acids from enzyme extracts using two different buffers for various polymers as described herein and prior art precipitants.

The general usefulness of the class of cationic polymers of the present invention for removing nucleic acids and generally "cleaning-up" crude bacterial extracts, is demonstrated by testing the following spectrum of polymers of this invention as precipitants. The precipitants included copolymers containing secondary (B), tertiary (D,F), and quaternary (E,G) amines. The polymers were tested in two buffers, 0.15 M Tris-Cl, pH 8.5, and DTT buffer, and the results are presented in FIGS. 5A and B, respectively PEI, protamine sulfate (P SO$_4$) and manganese chloride are also included as precipitants for comparison.

Under the condition of this experiment all of the polymers tested, except for polymer No. 11, removed nucleic acids from solution. Some removal of aspartase activity was detected in either buffer with the concentration of polymer used (0.2 mg per mg protein). However, enzyme levels were lower in DDT-buffered samples than in similar Tris-buffer samples, and more enzyme activity was lost from samples containing either buffer when a polymer containing 100 percent of quaternary ammonium salt (G) was used as compared to extracts exposed to other polymers. The patterns of enzyme activity and nucleic acid precipitation by these synthetic polymers compared very well with the patterns found when protamine sulfate was the precipitant.

Manganese chloride was not very effective in precipitating nucleic acid from the extract containing Tris buffer, while it removed all of the aspartase activity from solution. The precipitated fraction of the samples was not examined for activity. Enzyme activity also was lost from the DDT-buffered sample with manganese chloride addition but not as completely as from the previous sample. It is known that manganese chloride addition to cell extracts results in large losses of enzyme activity, and as reported, this effect is a major problem in using manganese as a precipitant.

EXAMPLE 4

Effect of pH on Precipitation

Figure 6:
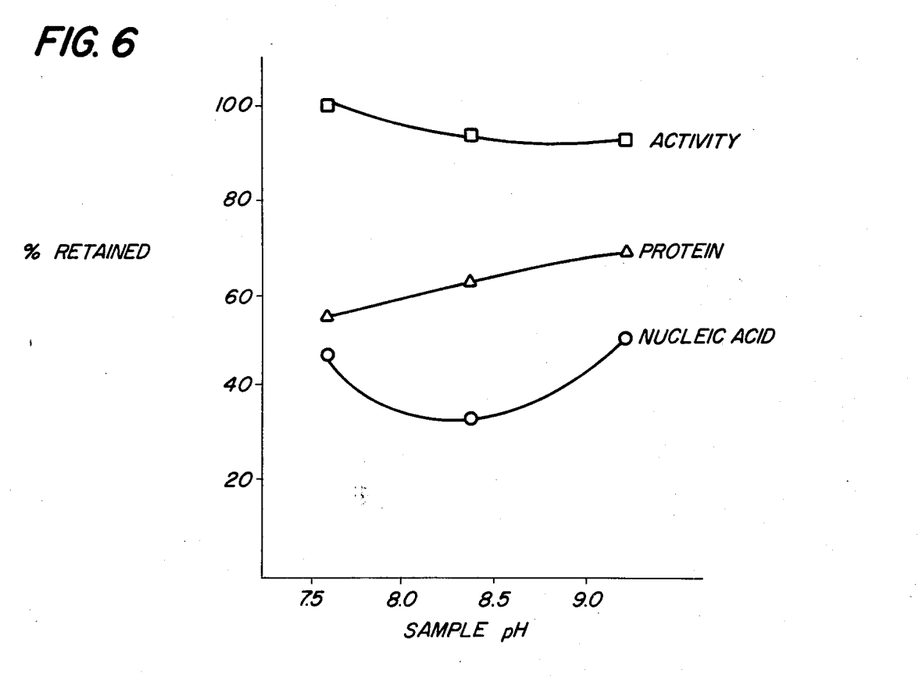
FIG. 6 is a graph illustrating the effect of pH on the effectiveness in removing nucleic acids and non-active proteins from an enzyme extract using a polymer as described herein.

The pH of crude extract was varied over the pH range 7.5 to 9.2, and patterns of precipitation of nucleic acids and proteins, and loss of aspartase activity was determined (FIG. 6). Polymer 12, at 0.2 mg per mg protein, was the polymer used in this example. No significant loss of enzyme activity was found at the pH values tested. Some modification in the extent of removal of nucleic acids and proteins was indicated; that is, the removal of both materials decreased as the pH of the extract become more alkaline. This could mean that at the higher pH some of the secondary amines of polymer 12 have been deprotonated, and therefore, the charge density of the polymer has decreased. This would lower the tendency of the polyelectrolyte to complex with nucleic acids and proteins. Other polymers, however, especially those containing quaternary amines, are not similarly affected by elevated pH values, and thus the data with polymer 12 were interpreted to show no pH effect for the polyelectrolyte technique.

EXAMPLE 5

Effect of Protein Concentration on Precipitation

Figure 7:
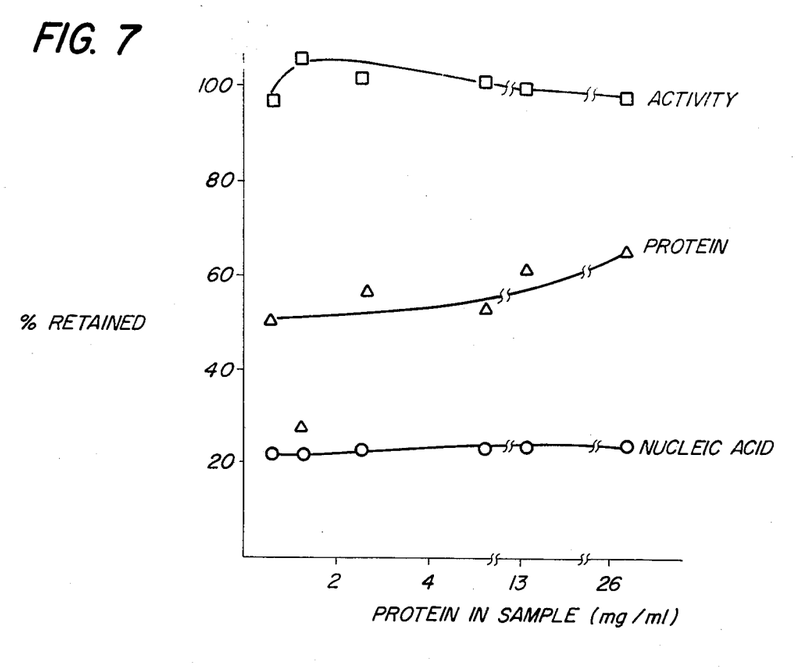
FIG. 7 is a graph illustrating the effect of protein concentration of the effectiveness of a polymer as described herein in removing nucleic acids and non-active protein from an enzyme extract.

It is well known that the effectiveness of protamine sulfate as a precipitant can be negatively influenced by increases in protein concentration of samples. This is not the case when polymer 12 was tested with extracts where protein concentration was varied from 0.6 to 26.4 mg per ml (see FIG. 7). Nucleic acid content remained 0.09 mg per mg protein for all untreated samples. Polymer 12 was added to each sample at a constant ratio to the protein (0.2 mg polymer per mg protein). No decrease in effectivenss of this polymer to precipitate nucleic acids was observed with changes in protein concentration, while approximately 80 percent of the nucleic acids were removed. No loss of aspartase activity was found following exposure to the polymer in any of the samples. A slight decrease in the removal of protein was observed at the higher protein levels,

EXAMPLE 6

Effect of Buffer Concentration on Precipitation

Figure 8:
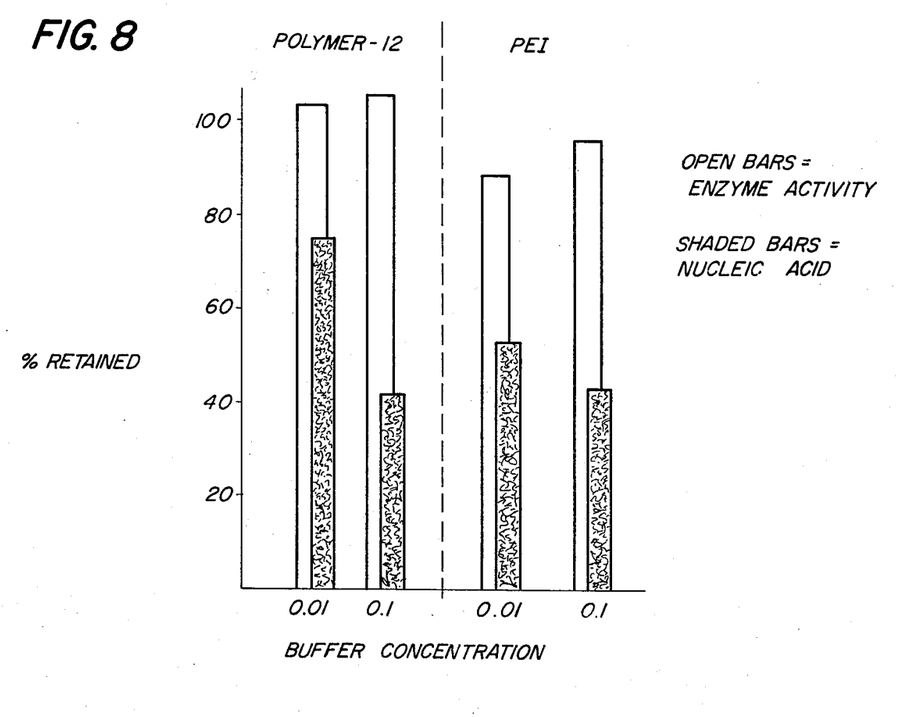
FIG. 8 is a graph comparing the effect of buffer concentration of nucleic acid removal and retention of enzyme activity for a polymer as described herein and polyethyleneimine, PEI.

British Pat. No. 1,298,431 reports that buffer concentration influences the ability of PEI, a synthetic polyelectroylte, to precipitate nucleic acids and proteins. At high salt concentrations (0.05 M phosphate buffer, pH 7.0), nucleic acids were precipitated selectively, while at lower salt concentrations (0.01 M phosphate buffer, pH 7.0), proteins were precipitated also. Such a trend was demonstrated, but not as conclusively, with data presented in FIG. 8. This moderate response, not totally precipitating the enzyme, probably was due to the low level of polymer used here (0.1 mg per mg of protein). As with other synthetic cationic polymers tested, PEI also had a polymer concentration dependence for maximum nucleic acid or protein precipitation. In addition, a comparison of the effectiveness of polymer 12 at two buffer concentrations is presented in the FIG. 8. Unlike PEI, polymer 12 did not decrease aspartase activity in the extract at the lower buffer concentration. Nucleic acid precipitation, however, was more efficient with polymer 12 at 0.1 M Tris-Cl than it was at 0.01 M buffer.

EXAMPLE 7

Molecular Weight Distribution of Some Polymer Samples

The molecular weight distributions of some polymer samples have been determined by aqueous exclusion chromatography. The analytical procedure consisted of diluting 0.1 ml of the polymer dope, as received, with 10 ml of eluant (0.1 M aqueous NaCl at pH 2.5). The solution was chromatographed on a series of five columns packed with CPG-10 porous glass of porosities 2000, 1400, 370, 175 and 75 A. The packings had previously been derivatized with the silane reagent γ-aminopropyltriethoxy silane. The eluate was monitored with a Waters R403 differential refractometer and a Varian 635 spectrophotometer at $\lambda = 220$ nm.

Polydextran equivalent number average and weight average molecular weights for the samples are given in Table I below.

Table I

| Polymer | $\overline{M}N$ | $\overline{M}w$ | $\overline{M}w/\overline{M}N$ | Inherent Viscosity, $\eta$ (.1M NaCl) |
|---|---|---|---|---|
| 6 | 659,000 | 1,350,000 | 2.05 | 1.17 |
| 6a | 588,000 | 2,050,000 | 3.49 | 1.90 |
| 9 | 195,000 | 609,000 | 3.11 | .59 |

These results appear consistent with the viscosity data discussed earlier.

Figure 9:
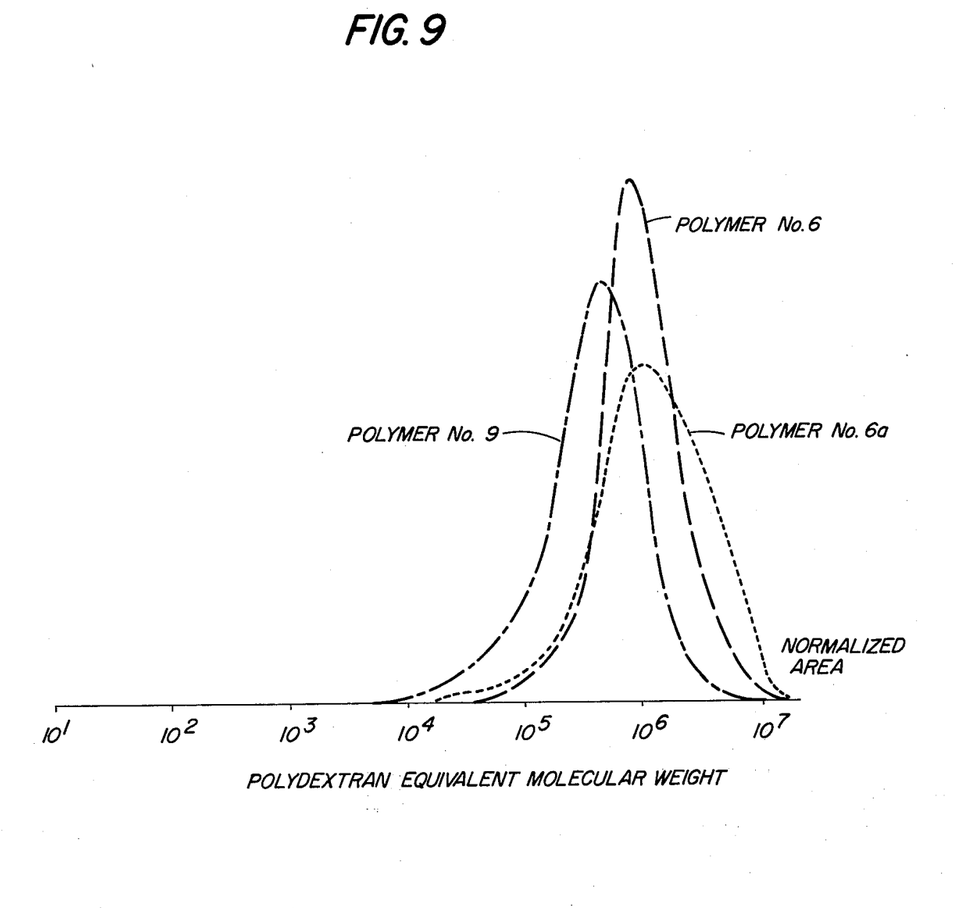
FIG. 9 is a graph illustrating the polydextran equivalent molecular weight distribution for certain polymers as described herein.

Computer-drawn curves showing the polydextran equivalent molecular weight distributions for the polymers are shown in FIG. 9. They indicate that all of the polymer molecules of the No. 6 and 6a polymer samples and that about 90 percent of the polymer molecules of polymer No. 9 are essentially larger than a polydextran molecule of molecular weight 100,000.

EXAMPLE 8

Effect of Several Polymers on a Variety of Microorganisms

A variety of microorganisms, listed in Table II, were grown in nutrient broth for 24–48 hours at 30° C. Cells were harvested by centrifugation (27,000 × g for 15 minutes), suspended in approximately 9 volumes of 10 mM Tris-Cl buffer, pH 7.5 (S. faecalis cells were suspended in 10 mM sodium acetate, pH 5.0), and sonically disrupted. Residual cells and debris were removed by centrifugation as above, and the supernatant fraction was used in the studies. Protein and nucleic acid content of each fraction were estimated by the 280/260 spectrophotometric method. Enzyme activity was measured by standard spectrophotometric techniques, and is expressed as units per ml enzyme sample, where 1 unit converts 1 μmole of substrate per min at 37° C. Following centrifugation, the cell-free extract was supplemented with 0.1 mg of indicated polymer per mg protein. The solution was mixed for 20 minutes at 4° C then centrifuged (27,000 × g for 15 minutes) to precipitate the complexed material. The clear supernatant was assayed, for enzyme, protein, and nucleic acid content as described above. The results are presented in Table II.

Table II

| Source | Polymer | Amount Retained, % | | |
|---|---|---|---|---|
| | | Enzyme Activity | Nucleic Acid | Protein |
| M. flavus | Catalase | | | |
| | ** | 100 | 100 | 100 |
| | 12 | 103 | 50 | 68 |
| | 4 | 103 | 50 | 74 |
| | 6 | 4 | 25 | 16 |
| B. megaterium | Catalase | | | |
| | ** | 100 | 100 | 100 |
| | 12 | 95 | 28 | 65 |
| | 4 | 105 | 32 | 85 |
| | 6 | 37 | 48 | 52 |
| P. testeroni | Catalase | | | |
| | ** | 100 | 100 | 100 |
| | 12 | 96 | 15 | 42 |
| | 4 | 34 | 16 | 23 |
| | 6 | 73 | 67 | 87 |
| S. faecalis | Lactate Oxidase | | | |
| | ** | 100 | 100 | 100 |
| | 12 | 115 | 31 | 73 |
| | 4 | 125 | 23 | 61 |
| | 6 | 123 | 17 | 27 |

Table II-continued

| Source | Polymer | Amount Retained, % | | |
|---|---|---|---|---|
| | | Enzyme Activity | Nucleic Acid | Protein |
| | | α-glycero-phosphate Oxidase | | |
| S. Faecalis | ** | 100 | 100 | 100 |
| | 12 | 108 | 31 | 73 |
| | 4 | 108 | 23 | 61 |
| | 6 | 95 | 17 | 27 |

**Control - no polymer

While the present invention has been described in detail with particular reference to certain preferred embodiments thereof, it will be appreciated that those skilled in the art may make modifications and extensions within the spirit and scope of this invention.

We claim:

1. A method for purifying a microbial enzyme extract, comprising the step of precipitating nucleic acids and unwanted protein by adding to the extract an effective amount of a water-soluble, cationic polymer comprised of a cationic monomer having the formula wherein $R_1$ is a hydrogen atom or a lower alkyl group, and $R_2$ is a nitrogen containing group capable of carrying a positive electrical charge when the polymer is dissolved in an aqueous solution having a pH value not greater than about the pKa of the polymer.

2. The method for purifying a microbial enzyme extract as defined in claim 1 wherein said cationic monomer comprises at least 10 percent by weight of the polymer.

3. The method for purifying a microbial enzyme extract as defined in claim 1 wherein said polymer further comprises a nonionic vinyl monomer.

4. The method for purifying a microbial enzyme extract as defined in claim 1 wherein said polymer is added to the extract in an amount from about 0.01 to about 0.5 mg per mg of protein in the extract.

5. The method for purifying a microbial enzyme extract as defined in claim 1 wherein said cationic monomer is selected from the group consisting of N-methyl-2-aminoethyl methacrylate hydrochloride, 1-vinylimidazole, 2-(N,N,N-trimethylammonium)ethyl methacrylate chloride, 2-(N,N-dimethylamino)ethyl methacrylate, 2-(N,N,N-triethylammonium)ethyl methacrylate methosulfate, and 2-hydroxy-3-(N,N,N-trimethylammonium)propyl methacrylate chloride.

6. A method for purifying a microbial enzyme extract, said method comprising the step of precipitating nucleic acids and unwanted protein by adding to the extract an effective amount of a water-soluble, cationic polymer comprised of a cationic monomer having the formula wherein:
$R_1$ is a hydrogen atom or a lower alkyl group; and
$R_2$ is selected from the group consisting of where X is an anion.

7. The method of purifying a microbial enzyme extract as defined in claim 6 wherein said cationic monomer comprises at least 10 percent by weight of the polymer.

8. The method of purifying a microbial enzyme extract as defined in claim 6 wherein said polymer further comprises a nonionic vinyl monomer.

9. The method for purifying a microbial enzyme extract as defined in claim 6 wherein said polymer is added to the extract in an amount of about 0.01 to about 0.5 mg per mg of protein in the extract.

10. A method for purifying a microbial enzyme extract, said method comprising the step of precipitating nucleic acids and unwanted protein by adding to the extract an effective amount of a water-soluble, cationic polymer comprised of a monomer having the formula wherein:
$R_1$ is a hydrogen atom or a lower alkyl group; and
$R_2$ is selected from the group consisting of where X is an anion, said monomer comprising at least 10 percent by weight of said polymer and said polymer being added to the extract in an amount of from about 0.01 to about 0.5 mg per mg of protein in the extract.

11. The method of purifying a microbial enzyme extract as defined in claim 10 wherein said polymer further comprises a non-charged vinyl monomer.

12. The method of purifying a microbial enzyme as described in claim 11 wherein said vinyl monomer is acrylamide or a hydroxyalkyl acrylate.

13. The method of purifying a microbial enzyme extract as defined in claim 10 wherein the polymer is added to the extract in an amount of from about 0.05 to about 0.2 mg per mg of protein in the extract.

14. The method of purifying a microbial enzyme as described in claim 13 wherein said polymer is further comprised of hydroxyalkyl acrylate monomer.

* * * * *

Disclaimer

4,055,469.—*Roy Eugene Snoke*, Webster; and *Gerald Wayne Klein*, Pittsford, N.Y. PURIFICATION OF MICROBIAL ENZYME EXTRACTS USING SYNTHETIC POLYELECTROLYTES. Patent dated Oct. 25, 1977. Disclaimer filed Feb. 15, 1983, by the assignee, *Eastman Kodak Co.*

Hereby enters this disclaimer to all claims of said patent.

*[Official Gazette May 3, 1983.]*